(12) United States Patent
Martinez et al.

(10) Patent No.: US 6,706,033 B1
(45) Date of Patent: *Mar. 16, 2004

(54) MODULAR ACCESS PORT FOR DEVICE DELIVERY

(75) Inventors: Lorraine Mangosong Martinez, Sunnyvale, CA (US); Jobert Balceta, San Jose, CA (US); Kevin Hahnen, Sarasota, FL (US); Bruce Addis, Redwood City, CA (US); Timothy J. Wood, Billerica, MA (US); Roman Turovskiy, San Francisco, CA (US); Richard O. Murphy, Mountain View, CA (US); Tracy D. Maahs, Santa Clara, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/365,650

(22) Filed: Aug. 2, 1999

(51) Int. Cl.[7] .................... A61M 29/00; A61M 25/00
(52) U.S. Cl. .................. 604/523; 600/130; 600/153; 604/264; 604/164.09
(58) Field of Search ................. 604/523, 264, 604/164.09, 167.01, 533, 534, 535, 539; 606/191, 194, 200; 600/130, 153

(56) References Cited

U.S. PATENT DOCUMENTS

| | | | |
|---|---|---|---|
| 5,776,111 A | | 7/1998 | Tesio |
| 5,951,521 A | | 9/1999 | Mastrototaro et al. |
| 6,090,072 A | * | 7/2000 | Kratoska et al. ....... 604/164.01 |
| 6,146,354 A | * | 11/2000 | Beil ........................... 604/28 |
| 6,152,910 A | * | 11/2000 | Agro et al. ................. 604/264 |
| 6,190,357 B1 | * | 2/2001 | Ferrari et al. .......... 604/102.01 |
| 6,206,849 B1 | * | 3/2001 | Martin et al. ............... 604/264 |
| 6,261,273 B1 | * | 7/2001 | Ruiz ........................... 604/284 |
| 6,280,432 B1 | * | 8/2001 | Turovskiy et al. ..... 604/164.09 |
| 6,328,730 B1 | * | 12/2001 | Harkrider, Jr. ............ 600/130 |
| 6,338,725 B1 | * | 1/2002 | Hermann et al. ....... 604/164.01 |
| 6,383,144 B1 | * | 5/2002 | Mooney et al. ............. 600/435 |

* cited by examiner

*Primary Examiner*—Henry Bennett
*Assistant Examiner*—Kathryn Odland
(74) *Attorney, Agent, or Firm*—O'Melveny & Myers LLP; John Christopher James

(57) ABSTRACT

Modular systems comprising a cannula and at least one access port adjacent to a distal end of the cannula provide insertion of one or more therapeutic or diagnostic devices into a vessel or cardiac tissue through a single incision site. Other embodiments include a vessel introducer or multi-port introducer. The devices can be operated in combination or independently. The systems can be employed to provide multiple therapies, including blood perfusion, filtration, aspiration, vessel occlusion, atherectomy, and endoscopic devices. Methods of using the system for vessel cannulation are also disclosed herein.

15 Claims, 21 Drawing Sheets

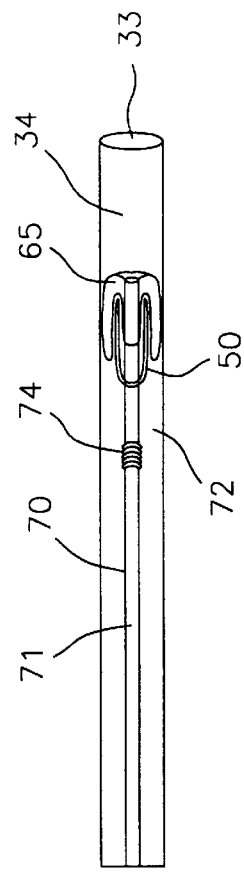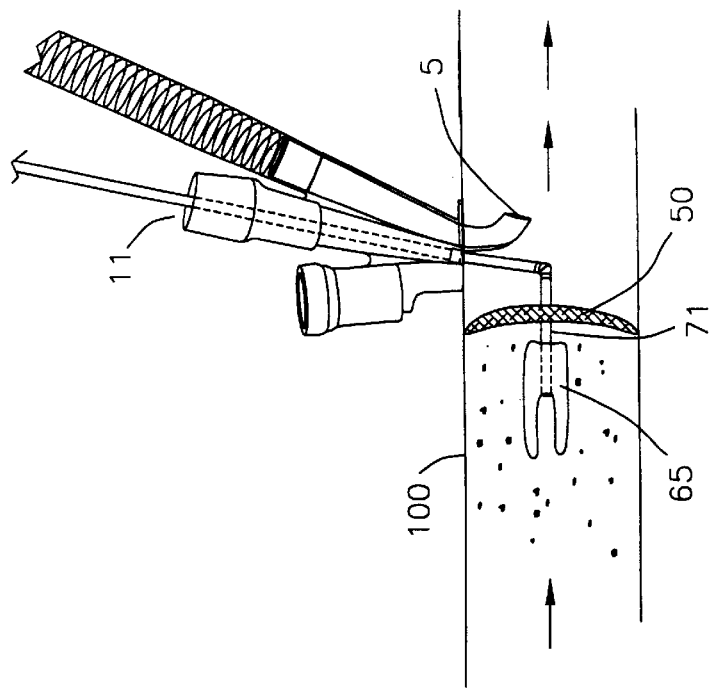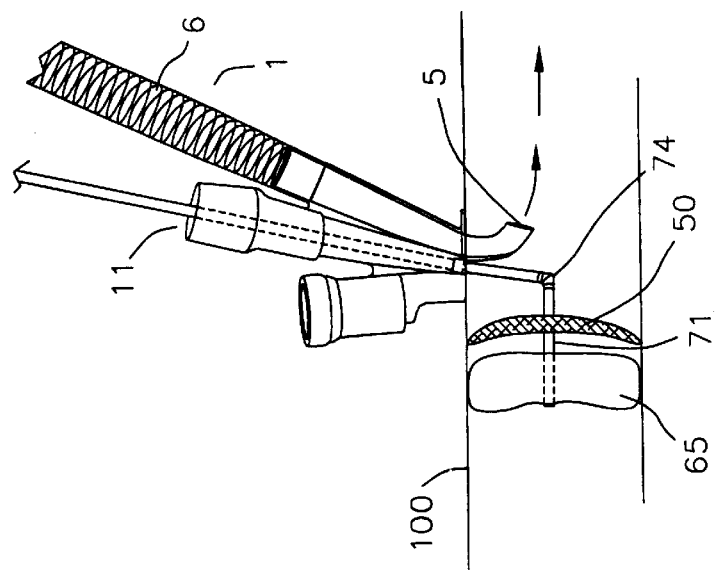

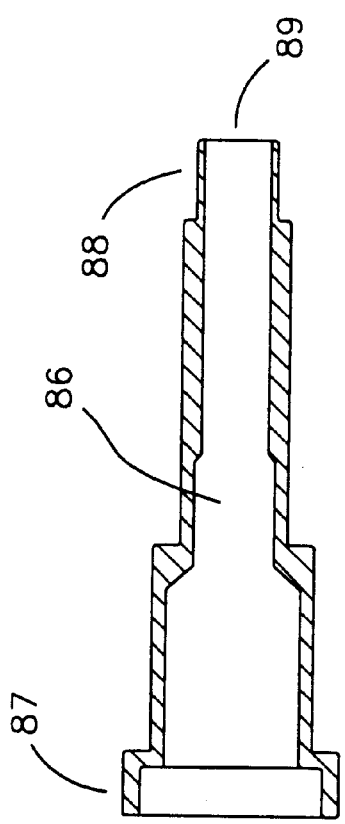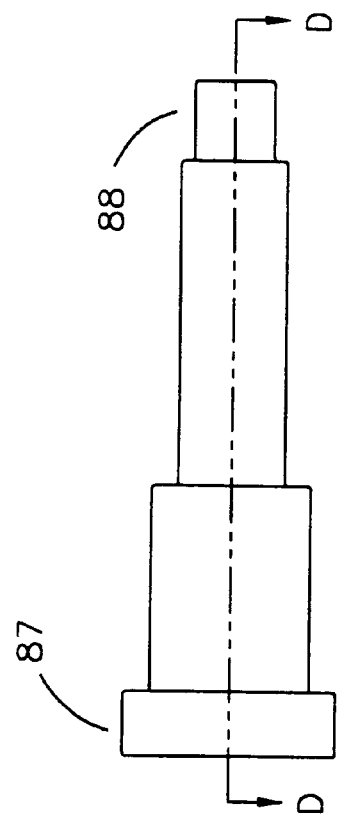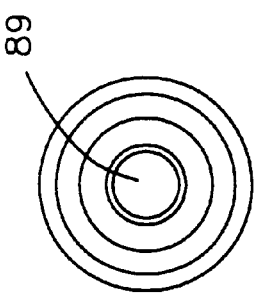

MODULAR ACCESS PORT FOR DEVICE DELIVERY

FIELD OF THE INVENTION

The present invention generally relates to a modular system for introducing therapeutic or diagnostic devices, such as a blood filter, occluder, atherectomy device, stents, angiographic catheters, and pressure monitors to a vessel or cardiac tissue. More particularly, the system delivers the devices independently or in combination through a single incision on the vessel or cardiac tissue via one or more access ports and lumens.

BACKGROUND OF THE INVENTION

During various cardiothoracic, pulmonary, and vascular surgeries, including coronary artery bypass grafting, heart valve repair or replacement, atrial or ventricular septal defect repair, angioplasty, atherectomy, aneurysm repair, and pulmonary thrombectomy, cannulation of a patient's vessel (s) are often required to provide vascular access for delivery of various diagnostic and therapeutic devices. In a conventional approach, separate incisions are needed for introduction of each medical device. For example, during coronary artery bypass grafting (CABG) surgeries, cardiopulmonary bypass is established by cannulation of the aorta to provide circulatory isolation of the heart and coronary blood vessels. Two incisions on the aorta may be required, i.e., one for insertion of the arterial cannula and another for insertion of a balloon occluder to provide coronary isolation from the peripheral vascular system. When cardiac arrest is desired, a third incision may be required on the aorta to introduce a catheter for delivering cardioplegic solution to the coronary arteries. Additional incisions may be required for insertion of other devices, such as a blood filter, pressure monitor, or atherectomy device. Once the incisions are made on the aorta, the devices often remain in the aorta throughout the entire procedure despite only being used intermittently, e.g., the cardioplegia catheter.

Due to significant mortality and morbidity associated with the conventional CABG surgeries from the use of cardiopulmonary bypass for circulatory support and the traditional method of access by median sternotomy, minimally invasive concepts recently have been adopted to make cardiothoracic procedures less invasive. Minimally invasive alternatives include the minimally invasive direct CABG procedure in which the operation is performed through minimal access incisions, eliminating cardiopulmonary bypass. The second alternative is to perform the procedure through minimal access incisions, and cardiopulmonary support is instituted through an extra thoracic approach, i.e., the port access approach. The third alternative is to perform the procedure on a beating heart which allows greater access for more extensive revascularization, i.e., the "off pump" sternotomy approach. In any of the minimally invasive alternatives, the space allowed for multiple instrumentation and device insertion is limited.

The disadvantages associated with the conventional or minimally invasive approach are that (1) by having multiple devices inserted in the aorta, the space available for the surgeon to perform procedures is limited, and (2) the aorta is traumatized as a result of multiple incisions, which may result in aortic dissection, aortic wall hematoma, and/or embolization of calcium plaque from the aortic wall. The greater the aortic trauma, the higher the perioperative morbidity a patient will endure.

New devices or systems are therefore needed which provide access to a patient's vessel and introduction of multiple diagnostic and therapeutic devices during cardiovascular procedures, thereby minimizing crowding caused by the multiple device insertions and trauma to the vessel wall.

SUMMARY OF THE INVENTION

The methods and systems of the present invention provide means of introducing a combination of multiple devices or instruments into a vessel through a single incision site, thereby reducing the number of incisions on the vessel and minimizing space crowding during vascular surgeries. More particularly, various devices and instruments can be inserted into the vessel through one or multiple lumens and access ports included in the modular access port systems, thereby minimizing the trauma of exchanging devices against the vessel wall. The methods and systems can be used in conventional or minimally invasive surgeries to provide any combination of the following functions: perfusion, drug delivery, fluid infusion, vessel occlusion, filtration, aspiration, venting, fluid diversion, venous return in cardiopulmonary bypass, atherectomy, fluid pumping, suturing, stapling, collagen or fibrin delivery, placement of pacing leads, use of angiographic catheters, angioplasty catheters, valvuoplasty catheters, electrode catheters, sizing tools, internal vessel segregating or isolating dams, endoscopic cameras, pressure monitors, shunts, stents, grafts, stent/grafts, vessel surfacing modalities, radioactive isotopes, graft delivery, and endoscopic devices. For example, devices traditionally introduced through the femoral artery (i.e., stents, atherectomy catheters, or angioplasty catheters) can also be introduced directly into the aorta, if deemed advantageous or beneficial to the patient.

In a first embodiment, the systems comprise a cannula having a distal end, a first access port adjacent to the distal end of the cannula, and a second access port adjacent to the first port. The ports and the distal end of the cannula are arranged substantially in a line. The distal end of the cannula is adapted for perfusion of blood, i.e. for use as an arterial cannula or venous return cannula in cardiopulmonary bypass. The cannula also has a proximal end adapted for attachment to a bypass-oxygenator machine, and a lumen adapted for perfusion of oxygenated or deoxygenated blood. Each of the first and the second access ports has a lumen extending from a proximal end to a distal end. The proximal ends of the ports are adapted to receive medical devices.

In another embodiment, the second port is adjacent to the distal end of the cannula and to the first port, such that the ports are arranged at the vertices of a triangle. Having the triangular arrangement may be preferred in minimally invasive procedures where surgical space is limited. A hemostatic valve may be included in the lumen of either or both of the access ports. The distal ends of the cannula and/or the access ports may include a suture flange for securing the system onto the vessel.

In still another embodiment, the systems comprise an elongate cannula having a distal end and an access port adjacent to the distal end of the cannula. The port has a lumen communicating with a distal end and a proximal end of the port. The proximal end and the lumen are adapted to receive at least one medical device, e.g., a blood filter and/or an occlusion catheter.

In still another embodiment, the systems comprise a vessel introducer having a tubular member and an obturator. The tubular member has a proximal end, a distal end, and a lumen, which may include a hemostatic valve in some embodiments. The obturator is removably insertable into the lumen of the tubular member. Medical devices, e.g., a blood filter, can be introduced through the proximal end and lumen of the tubular member.

In still another embodiment, the systems comprise a multi-port introducer having a first tubular member and a second tubular member mounted adjacent to the first member. Each of the first and second tubular members has a proximal end, a distal end and a lumen, which may include a hemostatic valve in some embodiments. The blood filter, for example, is removably insertable into the proximal port of either the first or the second member, allowing the other member to receive another medical device.

In a first method to provide insertion of medical devices and cannulation of a vessel or cardiac tissue, the distal ends of the cannula and the access ports described in the first embodiment are inserted through an incision on the vascular or cardiac tissue. For example, to provide arterial cannulation for cardiopulmonary bypass, the cannula is inserted through an incision on the aorta. A blood filter may be inserted through the first port, and an occlusion catheter having a balloon occluder may be inserted through the second port into the aorta. The blood filter is expanded to entrap embolic materials, calcium, myocardial tissue debris, or atheromatous plague, which arise as a result of introducing instrumentation or due to surgery. The occluder, e.g., a balloon occluder is expanded to provide circulatory isolation of the coronary vessels from the peripheral vascular system. The proximal end of the cannula is attached to a bypass-oxygenator machine to deliver oxygenated blood to the aorta. After the cardiopulmonary bypass is established, a surgical procedure can be performed on the heart and/or aorta.

In another method to provide insertion of medical devices and cannulation of a vessel or cardiac tissue, the distal ends of the cannula and the access port are inserted into a vessel or cardiac tissue. One or more medical devices are then inserted through an access port. For example, during arterial cannulation for cardiopulmonary bypass as described above, the blood filter and the occlusion catheter can be inserted sequentially through one access port into the aorta. After completion of the surgical procedure, one or both devices are removed from the access port. In situations where continuation of the cardiopulmonary bypass is desired post-operatively due to a patient's low cardiac output state, the blood filter may be removed, leaving the occlusion catheter and the cannula in the aorta. In this manner, multiple therapies and procedures are employed in combination or independently of each other.

The present invention also provides methods for introducing medical devices into a vessel without cannulation of the vessel. Using the vessel introducer described above, the distal end of the introducer is first inserted into the vessel. The obturator is removed and a medical device, e.g., a blood filter, is inserted through the proximal end of the introducer into the vessel. It should be noted that the medical device can be removed from the introducer and replaced with another device without altering the incision site or requiring another incision.

In still another method for introducing multiple devices into a vessel, the distal end of the multi-port introducer is inserted into the vessel. A medical device, such as a blood filter, is inserted into the proximal end of the first tubular member and advanced into the vessel. Another medical device is then inserted into the proximal end of the second tubular member and advanced into the vessel. Certain medical devices, such as a cardioplegia catheter, which are often used intermittently can remain in the introducer for the entire length of the procedure or be removed during part of the surgical procedure (to reduce space crowding), and then be reinserted into the introducer without altering the incision site.

It will be understood that there are several advantages to using the systems and methods disclosed herein for delivering medical therapies. For example, the systems (1) permit a combination of therapies to be employed through only one incision site, thereby minimizing trauma to the vessel wall, (2) allow multiple devices to be operated in combination or independently, (3) reduce the number of devices used concomitantly, thereby minimizing crowding in the surgical field, (4) can be employed in a variety of cardiac or vascular surgeries, and (5) can be used in minimally invasive procedures.

BRIEF DESCRIPTION OF THE DRAWINGS

FIG. 12A depicts another embodiment of the medical device carrying an occluder and a filter, where both the occluder and the filter are mounted on a catheter.

FIG. 12B depicts the device of FIG. 12A deployed in the aorta with expanded balloon occluder.

FIG. 12C depicts the device of FIG. 12A deployed in the aorta with deflated balloon occluder.

FIG. 15A depicts a lateral view of the tubular member shown in FIG. 14B.

FIG. 15B depicts a proximal view of the tubular member of FIG. 15A.

FIG. 15C depicts a distal view of the tubular member of FIG. 15A.

FIG. 15D depicts a cross-sectional view of the tubular member through section line D—D of the tubular member depicted in FIG. 15A.

DETAILED DESCRIPTION

Figure 1:
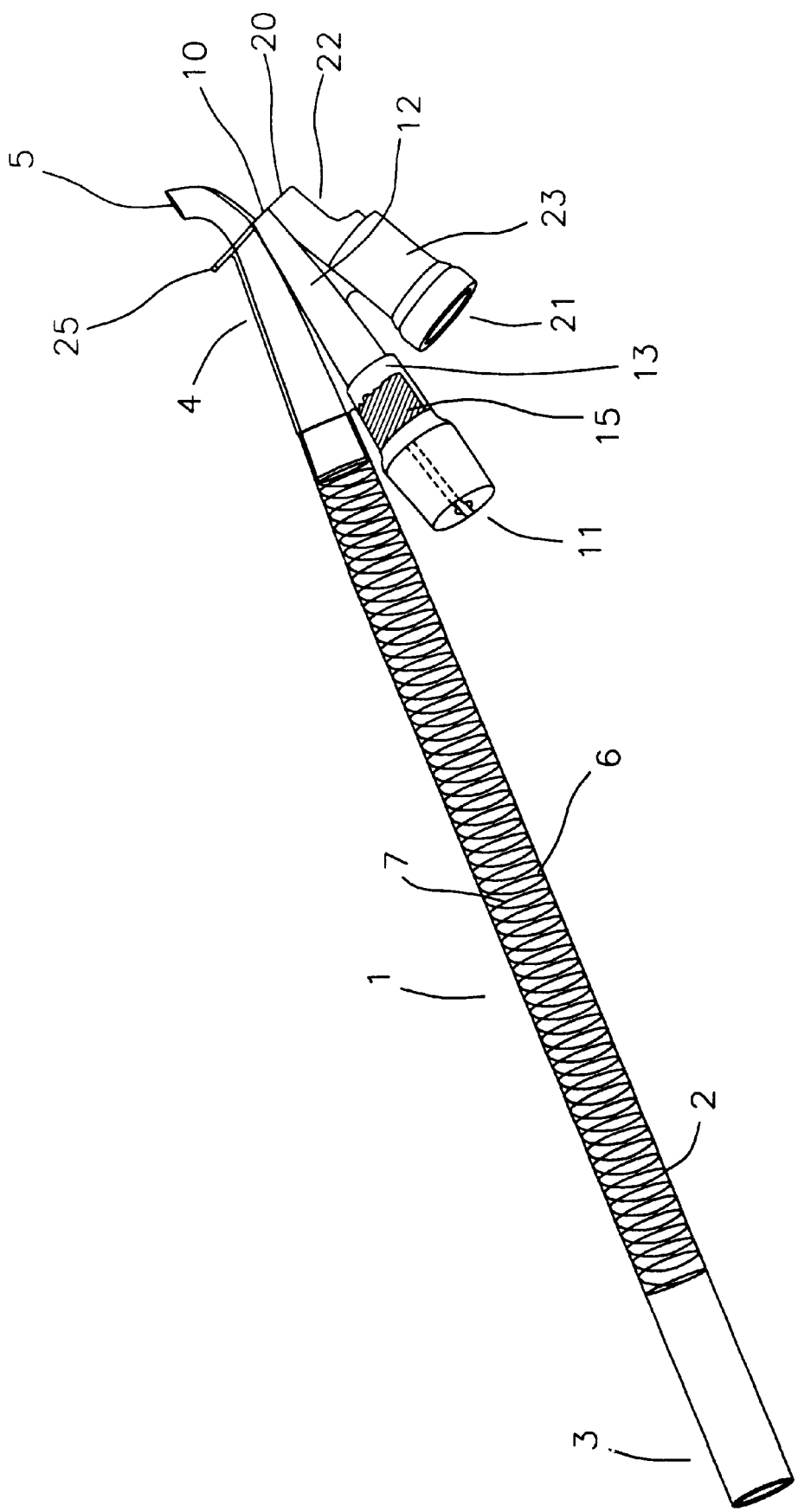
FIG. 1 depicts a lateral view of a cannula system for introduction of medical devices according to the present invention.
Figure 2:
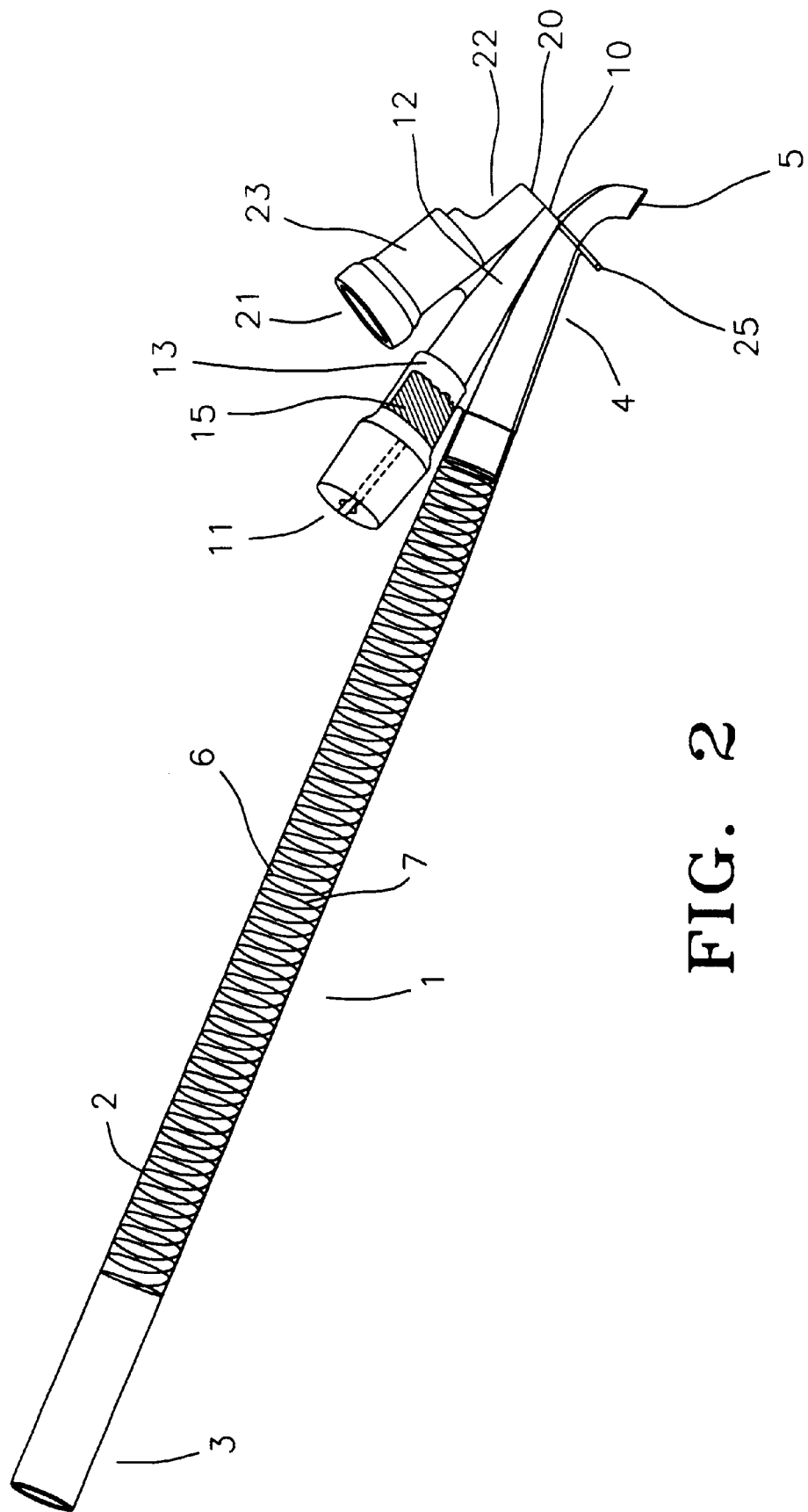
FIG. 2 depicts a lateral view of the cannula system of FIG. 1.
Figure 16C:
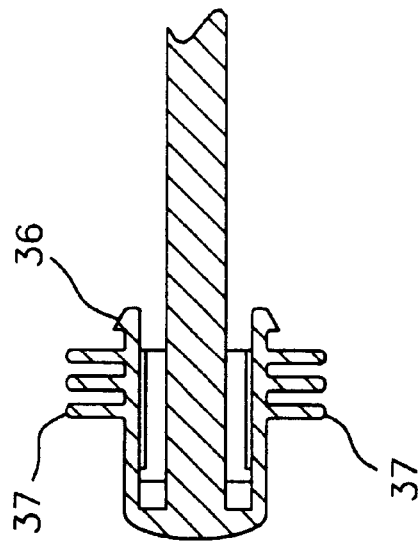
FIG. 16C depicts a cross-sectional view of a proximal region of the obturator through section line C—C of the obturator depicted in FIG. 16A.
Figure 16D:
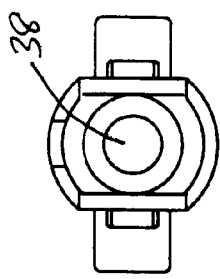
FIG. 16D depicts a distal view of the obturator shown in FIG. 16A.
Figure 16B:
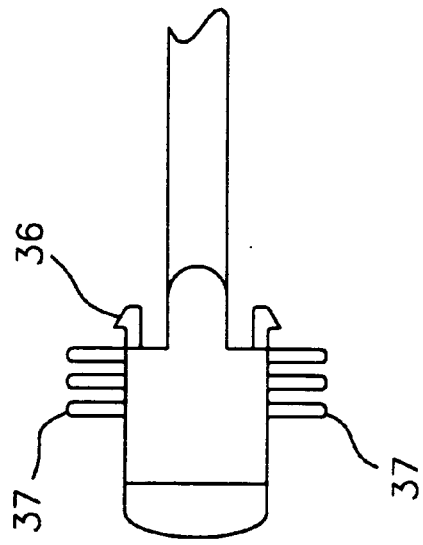
FIG. 16B depicts another lateral view of a proximal region of the obturator of FIG. 16A.
Figure 16A:
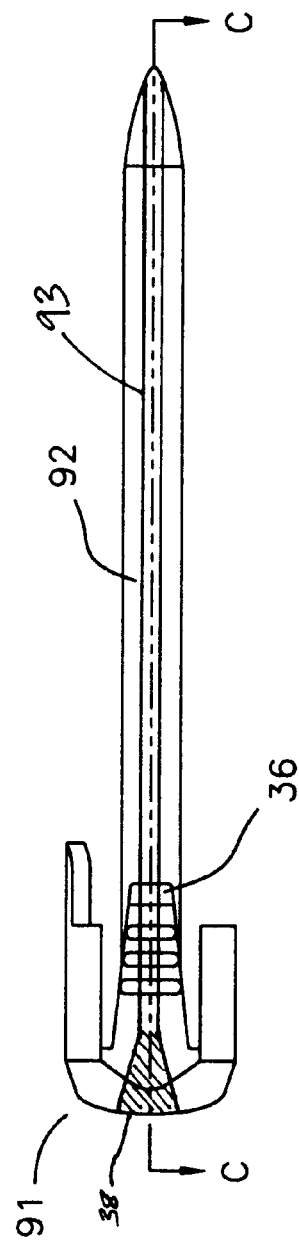
FIG. 16A depicts a lateral view of the obturator shown in FIG. 14B.

An embodiment of the cannula system for introducing medical devices into a patient's vessel or cardiac tissue is shown in FIGS. 1 and 2. In this embodiment, cannula 1 comprises elongate tubular member 2 having proximal end 3, distal end 4, and lumen 6. The lumen communicates with proximal end 3 and distal port 5 at the distal end. When used as an arterial cannula, the distal port is adapted to deliver oxygenated blood. When used as a venous return cannula, the distal port is adapted to receive deoxygenated blood. In FIG. 1, distal port 5 is shown angled relative to proximal end 3 for directing blood flow downstream the aorta more effectively, thereby reducing turbulent flow. The proximal end is adapted for attachment to a bypass-oxygenator machine. The wall of tubular member 2 further includes one or more helical wires 7 running the entire length of lumen 6 to prevent kinking while bending the cannula. First access port 10 is mounted adjacent to distal end 4 of the cannula, and second access port 20 is mounted adjacent to the first port. Each of the first and second access ports has, respectively, proximal end 11 and 21, distal end 12 and 22, and lumen 13 and 23. The proximal ends of the first and second access ports are adapted to receive therapeutic and/or diagnostic medical devices. It will be understood that, in use, the first and second access ports will be occupied by an obturator (e.g., as depicted in FIG. 16A) to prevent blood leakage prior to insertion of a medical device. Lumen 13 of the first access port further includes hemostatic valve 15. Suture flange 25 is included in distal end 4 of the cannula for suture placement.

Figure 3A:
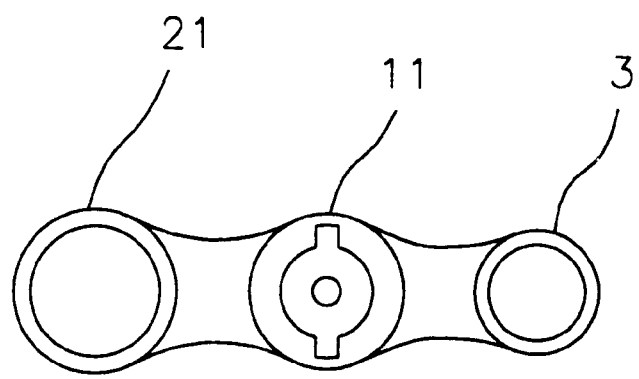
FIG. 3A depicts a frontal cross-sectional view of the cannula system of FIG. 1.
Figure 3B:
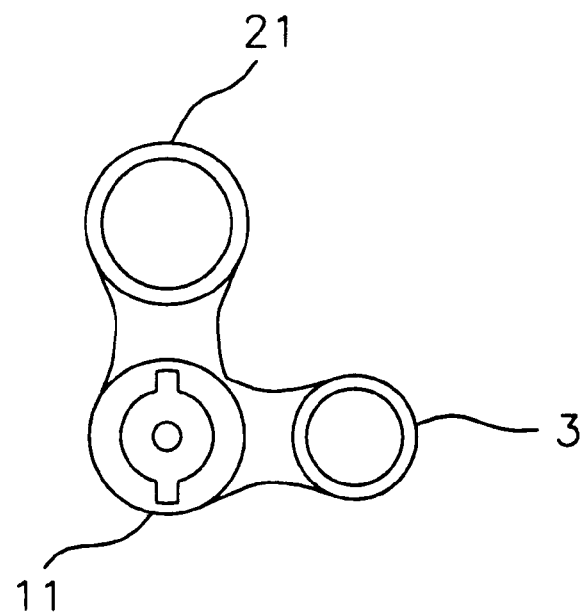
FIG. 3B depicts a frontal cross-sectional view of an alternative cannula system.

Proximal end 11 of the first port, proximal end 21 of the second port, and proximal end 3 of the cannula are arranged substantially in a line as in FIG. 3A which shows a frontal cross-sectional view of the cannula system of FIG. 1. Alternatively, proximal end 11 of the first port, proximal end 21 of the second port, and proximal end 3 of the cannula are arranged at the vertices of a triangle as shown in FIG. 3B. The access ports may be integral with the blood cannula.

Figure 6A:
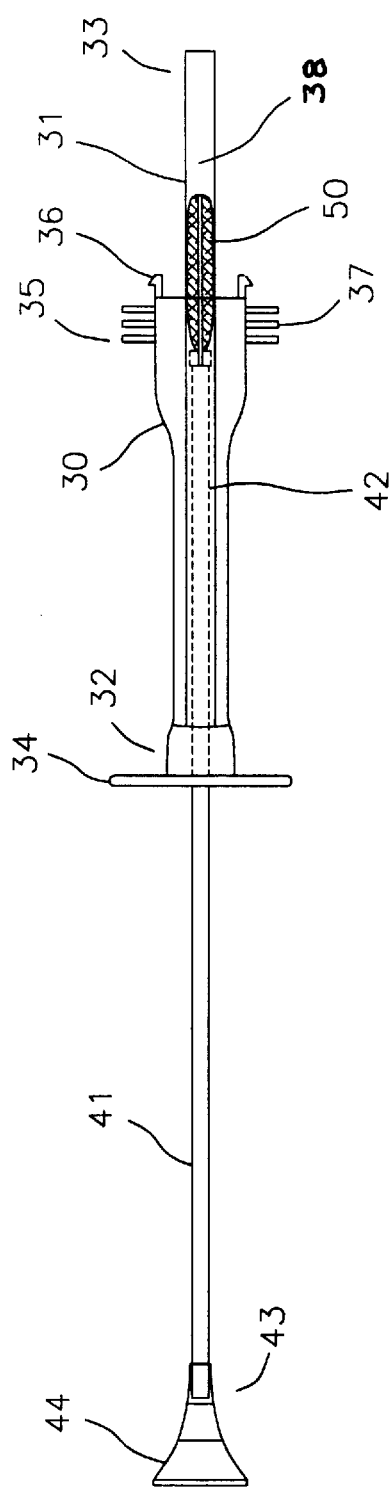
FIG. 6A depicts the medical device of FIG. 5 carrying a blood filter.
Figure 6B:
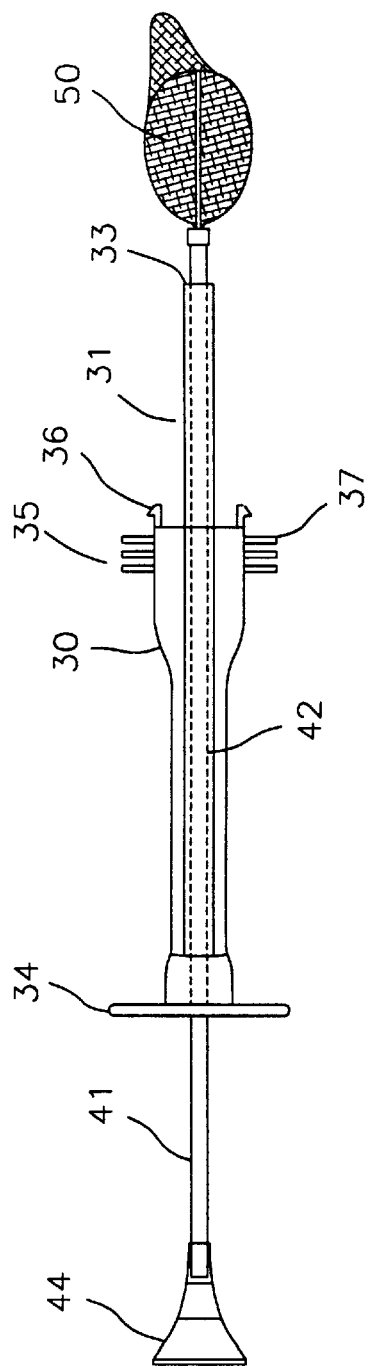
FIG. 6B depicts the deployment of the blood filter of FIG. 6B.

FIGS. 6A and 6B depict a blood filter which can be inserted into and removed from the proximal end of an access port. The blood filter has outer elongate tube 31 and inner elongate tube 32 which is slidably engaged within the outer tube. Outer tube 31 has distal end 33 and proximal end 34 which include proximal housing 35 connected proximally to collar handle 36.

Figure 4:
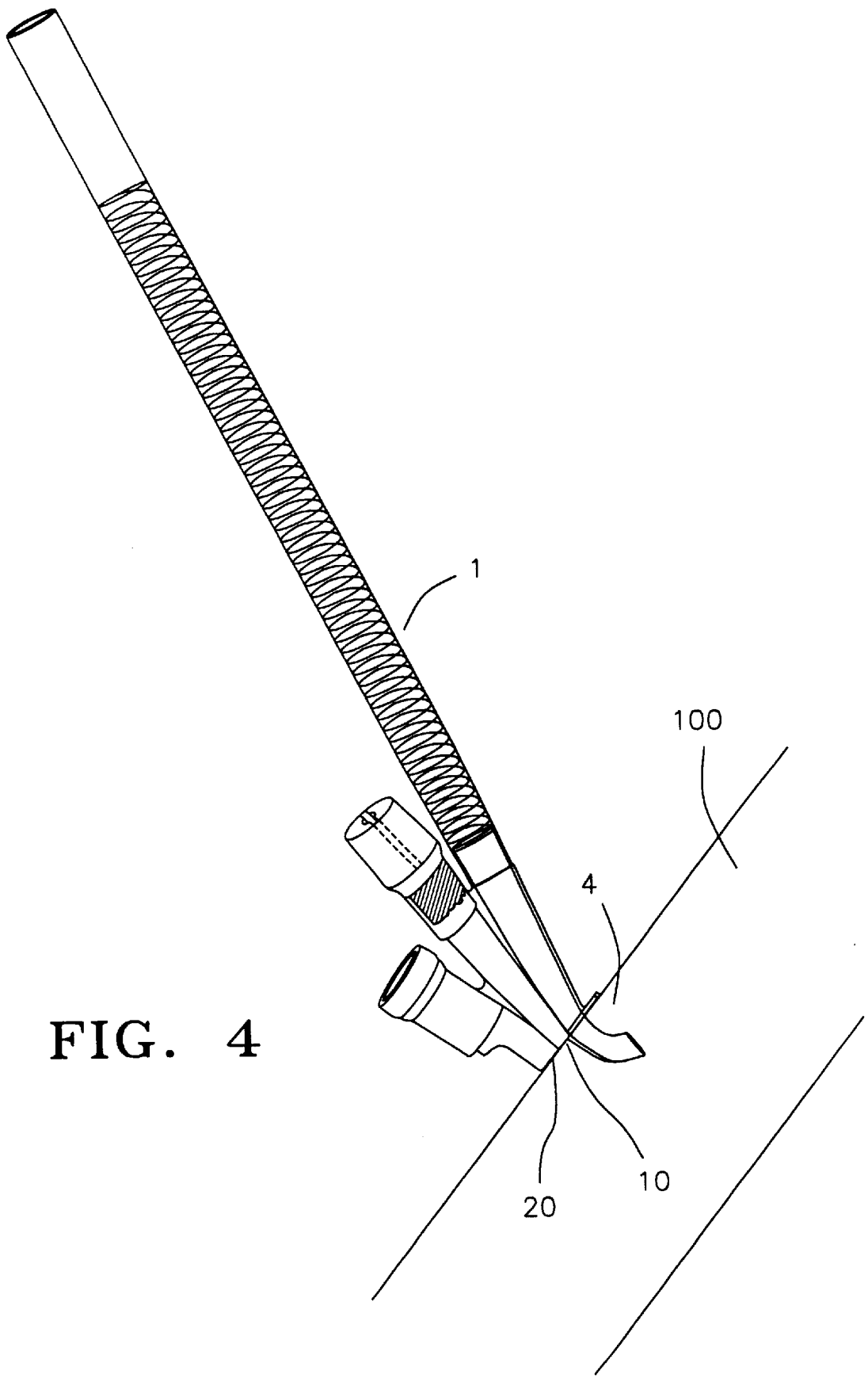
FIG. 4 depicts the cannula system of FIG. 1 inserted in an ascending aorta.

The cannula system of FIG. 1 can be used to cannulate, for example, a patient's aorta or right atrium for establishing cardiopulmonary bypass and to provide introduction of other medical devices in cardiovascular surgeries. In FIG. 4, the cannula system of FIG. 1 is shown inserted into a patient's ascending aorta. Distal end 4 of cannula 1 is first inserted through an incision on ascending aorta 100. Sutures can be placed on suture flange 25 to secure the cannula system onto the aorta. Medical devices can then be inserted into proximal ends 11 and 21 of ports 10 and 20, respectively, to carry out the following diagnostic or therapeutic functions: perfusion, drug delivery, fluid infusion, vessel occlusion, filtration, aspiration, venting, fluid diversion, venous return in cardiopulmonary bypass, atherectomy, fluid pumping, suturing, staples, collagen or fibrin delivery, pacing leads, angiographic catheters, angioplasty catheters, valvuloplasty catheters, electrode catheters, internal vessel segregating or isolating dams, endoscopic cameras, pressure monitors, shunts, stents, grafts, stent/grafts, vessel surfacing modalities, radioactive isotopes, and graft delivery.

Figure 5:
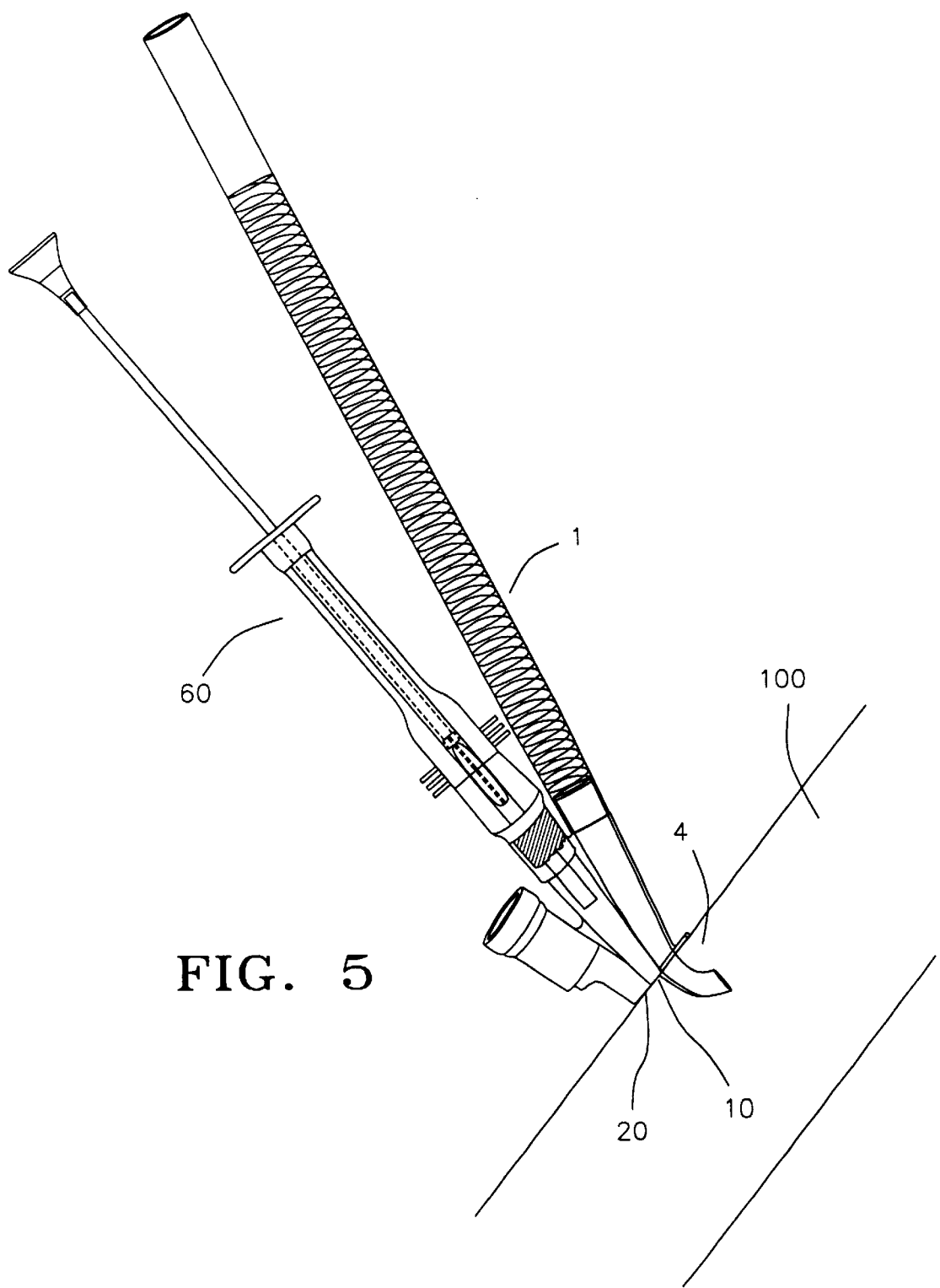
FIG. 5 depicts a medical device attached to the proximal end of the first access port of the cannula system of FIG. 1.

In FIG. 5, medical device 60 is shown attached to proximal end 11 of first port 10. The medical device is adapted for deployment of medical therapies, such as a blood filter, which is illustrated in FIGS. 6A and 6B. According to FIG. 6A, the device has housing 30, elongate tube 31 partially included in the housing, and elongate member 41. The tube has proximal end 32, distal end 33, and lumen 38. Distal region 42 of the elongate member, having blood filter 50 mounted distally, is slidably inserted within lumen 38 of the tube. The filter frame can be made of nitinol or other biocompatible material, such as stainless steel or plastic. The construction of the filter is described in more details in Barbut et al., U.S. Pat. No. 5,769,816, incorporated herein by reference. Porous plug 44, which is permeable to air but not to blood or fluid, is mounted on proximal end 43 of the elongate member. Collar handle 34 is attached to the proximal end of housing 30 and tube 31. Distal end 35 of the housing includes releasable engaging mechanism 36, such as a latch or fastener, and gripping members 37 for operating mechanism 36. The gripping members are mounted on opposite sides of the housing and can be constructed to have 1,2,3,4, or any other number on each side.

In use, the device is attached to a cannula system as shown in FIG. 5 by depressing members 37 on opposite sides of the housing so that mechanism 36 engages the proximal end of an access port. Elongate member 41 is advanced distally by exerting force on proximal end 43 while holding collar handle 34. As a result, filter 50 is advanced distal of opening 33 of tube 31 to be deployed in the aorta.

Figure 7A:
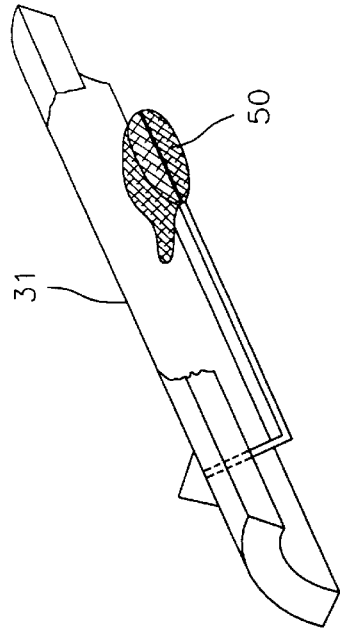
FIG. 7A depicts a cross-sectional view of an elongate tube housing a filter.
Figure 7B:
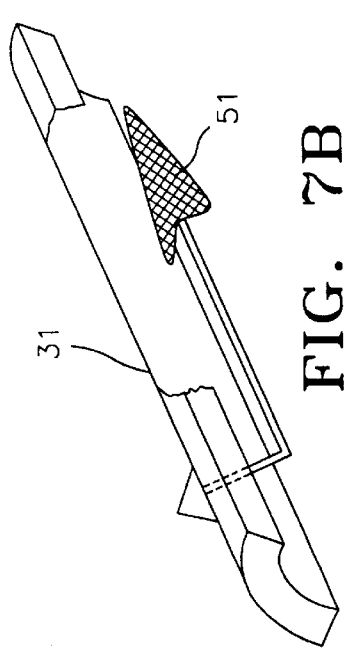
FIG. 7B depicts a cross-sectional view of an elongate tube housing a windsock.
Figure 7C:
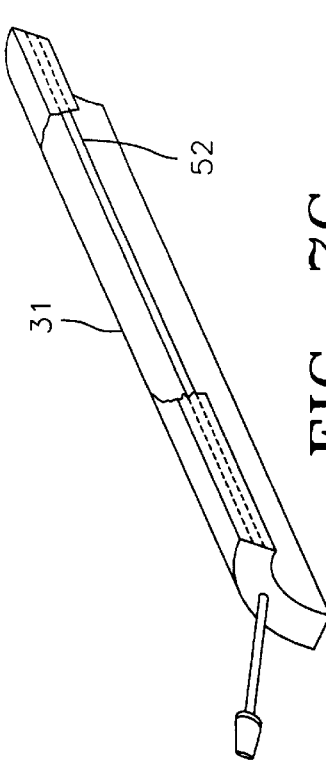
FIG. 7C depicts a cross-sectional view of an elongate tube housing an aspiration catheter.
Figure 7D:
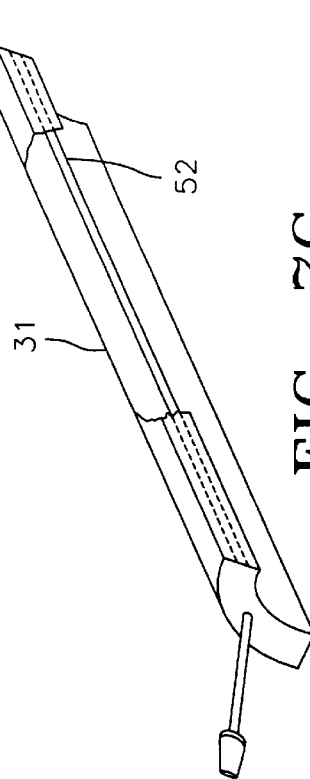
FIG. 7D depicts a cross-sectional view of an elongate tube housing a needle.
Figure 7E:
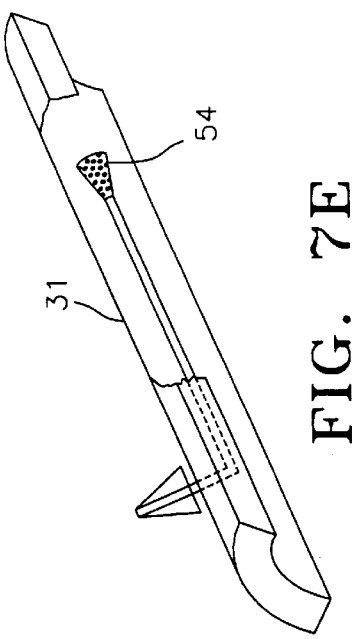
FIG. 7E depicts a cross-sectional view of an elongate tube housing a suction catheter.

Other embodiments of device 60 depicted in FIG. 5 can be used to deploy other medical therapies as shown in FIGS. 7A, 7B, 7C, 7D, and 7E. Filter 50 is shown carried within elongate tube 31 of the device in FIG. 7A. When deployed in a vessel, the filter entraps embolic materials, such as calcium, myocardial tissue debris, or atheromatous plagues which are generated upstream in the vessel. In FIG. 7B, windsock 51 is shown carried within tube 31. The design and use of a windsock is described in McKenzie et al., U.S. application Ser. No. 08/996,532, filed Dec. 23, 1997, incorporated herein by reference in its entirety. When the windsock is deployed in a vessel, blood flow downstream from the windsock is reduced. In FIG. 7C, aspiration catheter 52 is shown carried within tube 31. The aspirator can be used to remove vascular debris, for example, during coronary angioplasty or stent placement. In FIG. 7D, needle 53 is shown carried within tube 31 to provide for delivery of pharmaceutical agents, e.g., administering cardioplegia for cardiac arrest. In FIG. 7E, suction catheter 54 is carried within tube 31 to remove blood, fluid, air, or tissue debris during surgeries.

Figure 8:
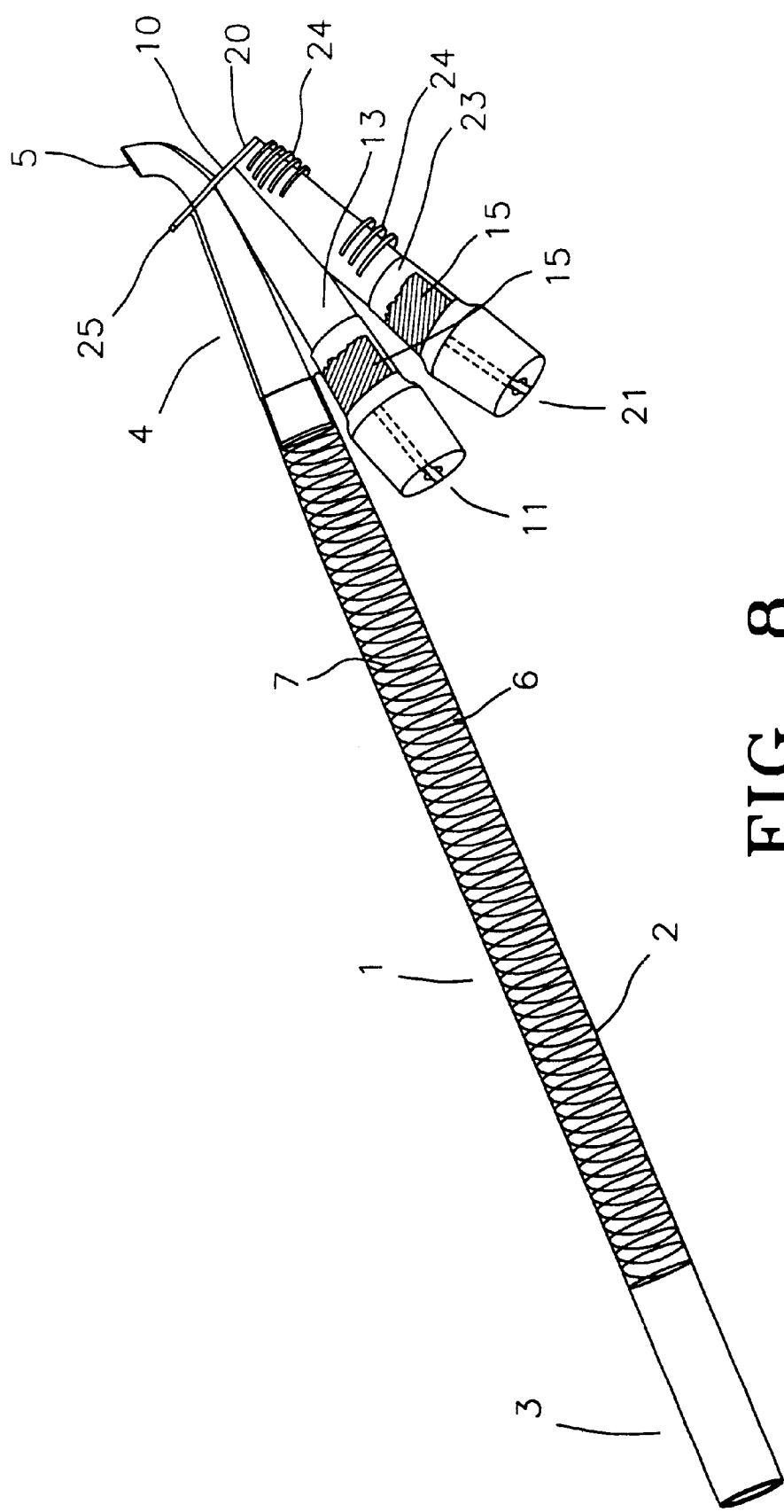
FIG. 8 depicts another embodiment of a cannula system for introduction of medical devices having two hemostatic valves.

FIG. 8 depicts another embodiment of the cannula system having two ports and two hemostatic valves. The cannula system of FIG. 8 is similar to that of FIG. 1 except that each of first access port 10 and second access port 20 communicates, respectively, with lumen 13 and 23 which include hemostatic valves 15. A distal region of port 20 also includes ridges 24 which minimize slippage of the cannula system from a surgeon's hand.

Figure 9:
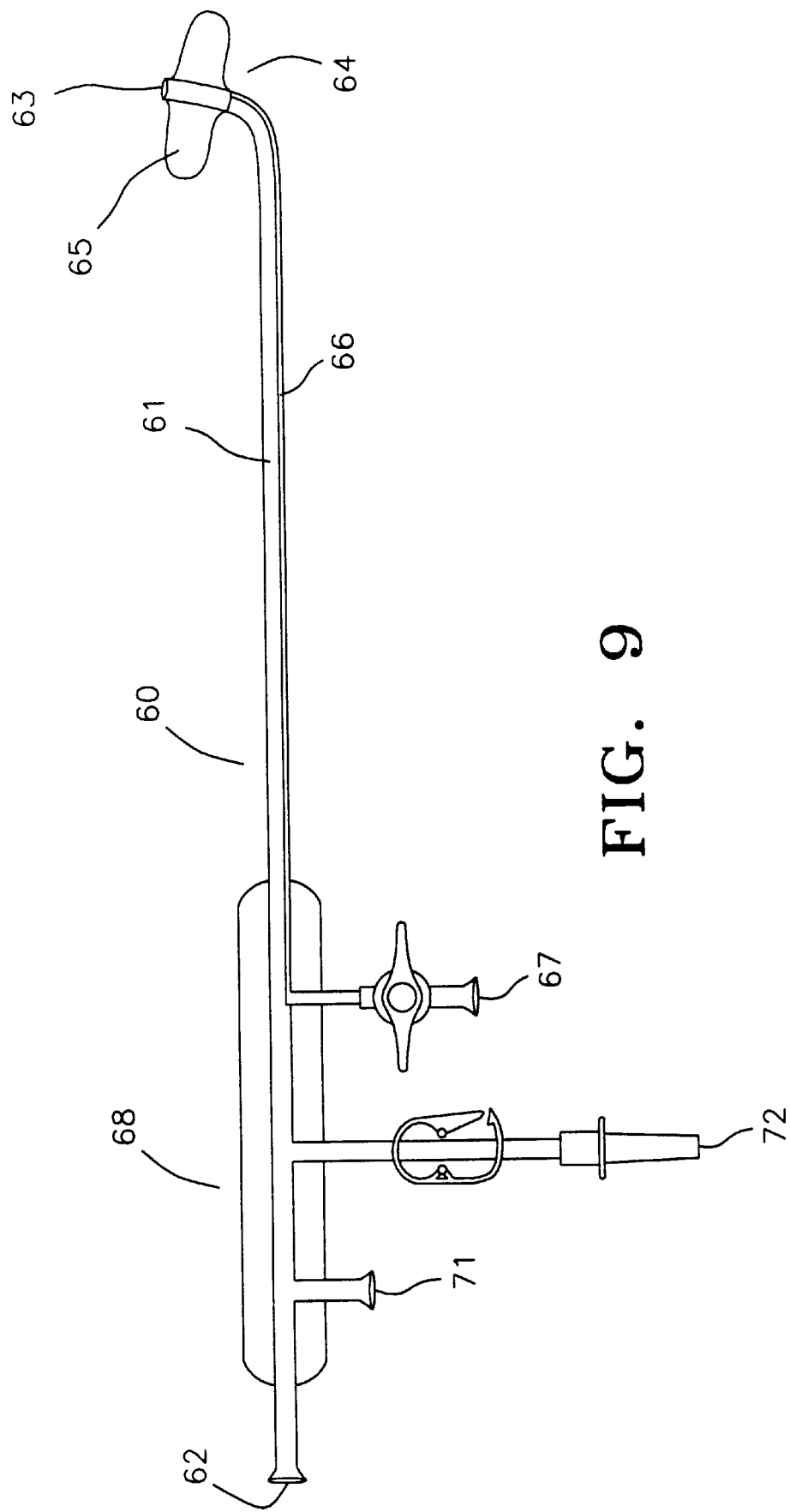
FIG. 9 depicts an embodiment of an occlusion catheter for isolating blood flow within a vessel.

FIG. 9 depicts an embodiment of an occlusion catheter for providing isolation of blood flow within a vessel. Catheter 60 has lumen 61 communicating with proximal port 62 and distal port 63 at distal end 64. Occluder 65, which may comprise an elastomeric balloon, is mounted on distal end 64 proximal to port 63. The occluder communicates with inflation lumen 66 and inflation port 67. Lumen 61 and proximal end 62 of the catheter are adapted for delivering fluid or a pharmaceutical agent, e.g., cardioplegia solution. Lumen 61 of the catheter also communicates with port 71 and port 72 at proximal region 68 of the catheter for infusing fluid or a pharmaceutical agent.

Figure 10:
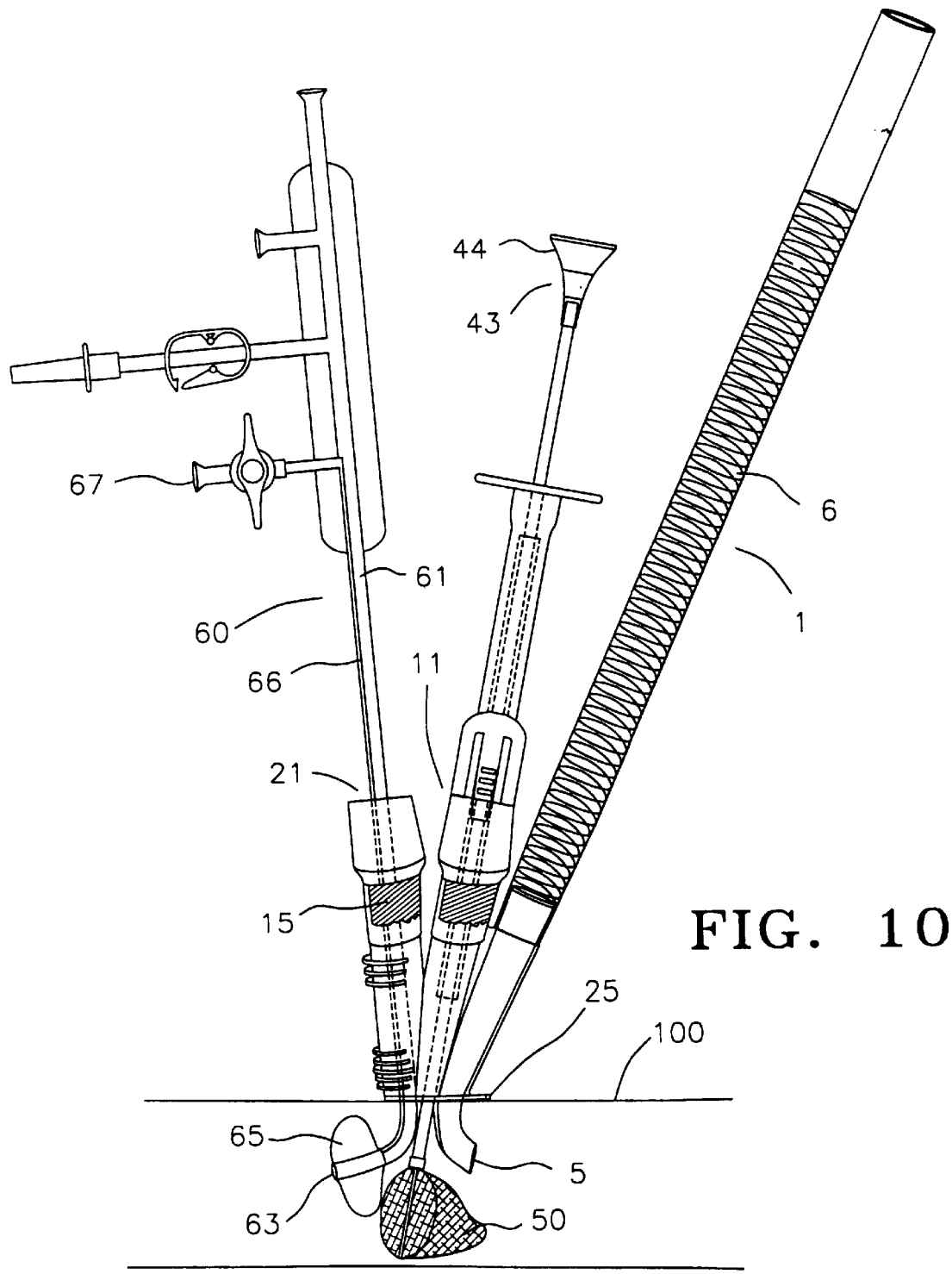
FIG. 10 depicts the cannula system of FIG. 8 having the devices of FIG. 6A and FIG. 9 deployed in the aorta through the access ports.
Figure 10A:
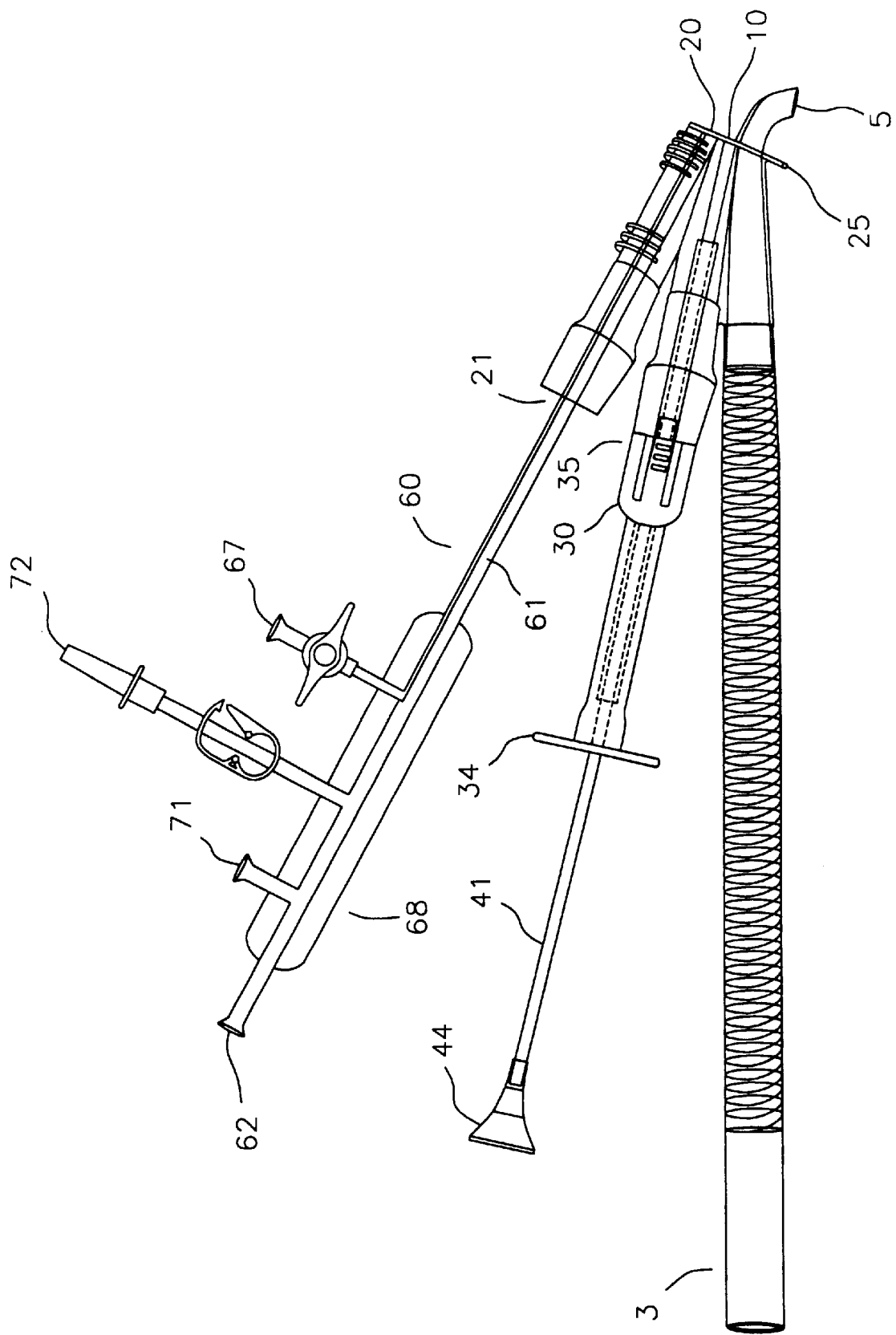
FIG. 10A depicts the cannula system of FIG. 8 having the devices of FIG. 6A and FIG. 9 attached to the proximal ends of the access ports.

In FIGS. 10A and 10, the device carrying a blood filter of FIG. 6A and the occlusion catheter of FIG. 9 are shown attached to the cannula system of FIG. 8. In FIG. 10A, occlusion catheter 60 is inserted through proximal end 21 and the lumen of access port 20. The distal end of the blood filter device is inserted through proximal end 11 and the lumen of access port 10. The releasable engaging mechanism mounted on distal end 35 of housing 30 is operated to lock the filter device onto proximal end 11 of the access port, thereby securing the device during deployment of the filter.

In using the cannula system of FIG. 10A, the distal end of the system is inserted through an incision on the vessel, e.g., ascending aorta 100, as shown in FIG. 10. The cannula system may be secured onto the aorta by placing sutures between suture flange 25 and the aortic wall. The proximal end 3 of cannula 1 is attached to a bypass-oxygenator machine. To establish cardiopulmonary bypass during cardiothoracic surgeries, for example, occlusion catheter 60 is advanced distally to deploy balloon occluder 65 in the aorta. Hemostatic valve 15 included in the lumen of the access port prevents blood loss through proximal end 21. The occluder is expanded by infusing air or fluid through inflation port 67 and lumen 66 to completely occlude the aortic lumen, thereby isolating the coronary circulation from the peripheral vascular system.

Cardioplegia solution can be delivered through port 63 upstream the aorta to the heart to achieve cardiac arrest. Simultaneous with infusion of cardioplegia, oxygenated blood is delivered through lumen 6 and port 5 of the cannula downstream in the aorta to perfuse the body organs. Blood filter 50 may be deployed prior to or during cardiopulmonary bypass by advancing proximal end 43 distally. Any blood that enters the distal end of the filter device will flow proximally toward porous plug 44, which allows air to escape but not blood. In this manner, the filter device is purged of gas and avoids introducing air emboli in the aorta.

After the surgeon has performed the cardiovascular procedures, cardiopulmonary bypass is discontinued by deflating balloon occluder 63 and stopping oxygenated blood infusion through cannula 1. As the occluder is deflated, embolic materials upstream the occluder, including calcium, atheromatous plaque, myocardial tissue debris, and thrombi, are trapped by filter 50. The filter is removed by retracting proximal end 43 of the device proximally, thereby removing vascular emboli.

Figure 11B:
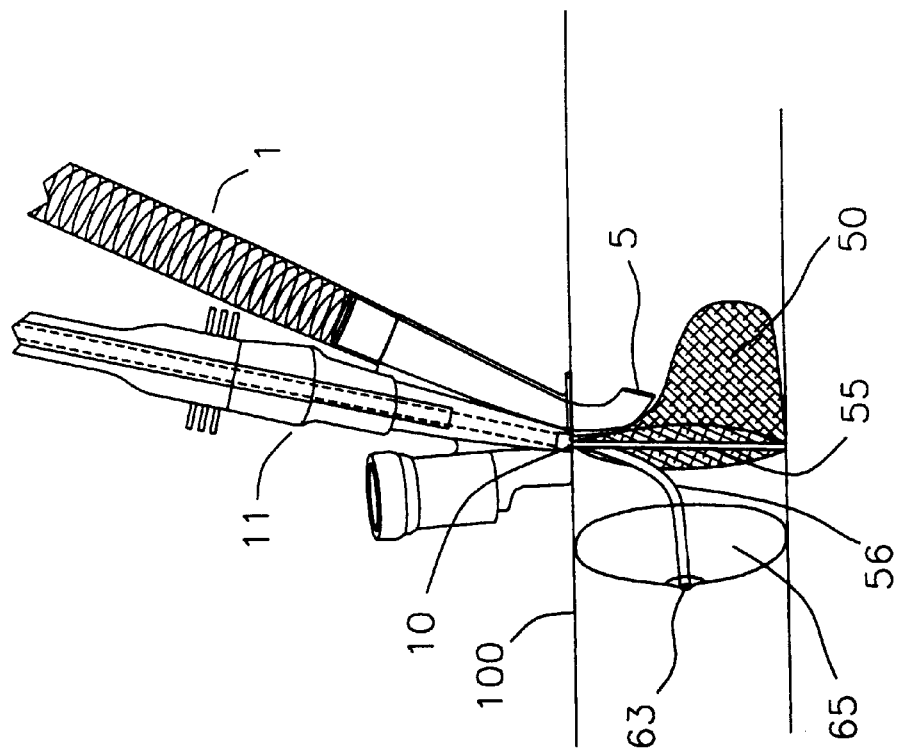
FIG. 11B depicts another embodiment of the medical device carrying an occluder and a filter having an occlusion catheter and the filter independently operable relative to each other.
Figure 11A:
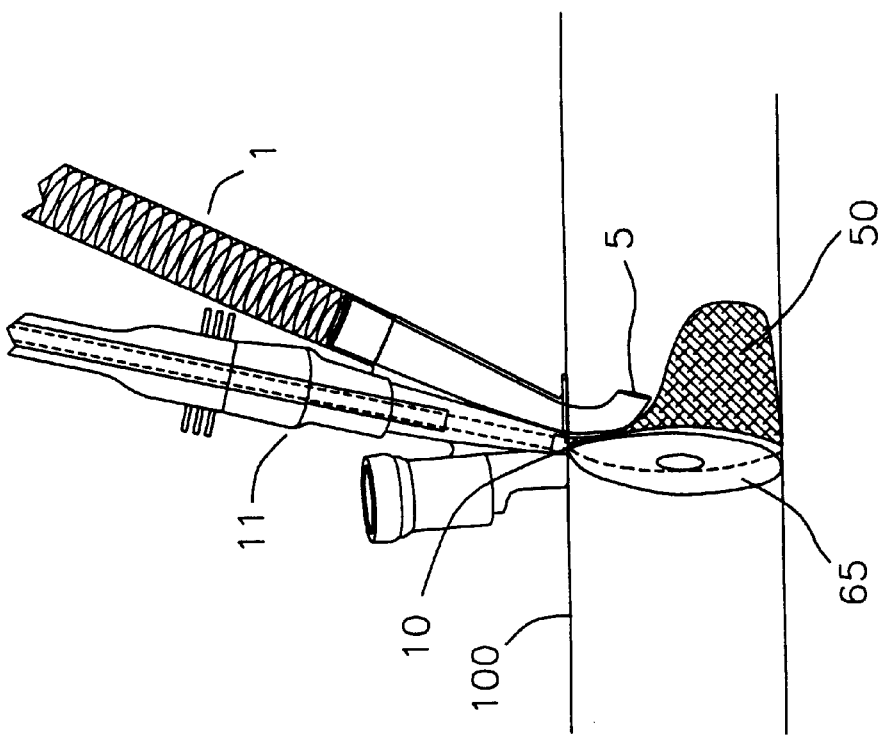
FIG. 11A depicts another embodiment of the medical device carrying an occluder and a filter having the balloon occluder mounted in the center of the filter.

FIGS. 11A and 11B depict other embodiments of medical devices carrying an occluder and blood filter for cardiopulmonary bypass. In FIG. 11A, the device carrying both balloon occluder 65 and filter 50 is inserted through proximal end 11 of access port 10. Occluder 65 is mounted inside the filter. When deployed in aorta 100, the occluder is expanded to occlude the aortic lumen during bypass and is deflated after cardiopulmonary bypass to allow embolic material upstream in the aorta to be captured in filter 50. After the surgeon has performed the cardiovascular procedure, occluder 65 and filter 50 are removed as a unit.

In FIG. 11B, another embodiment of the device carrying both balloon occluder 65 and filter 50 is shown inserted through proximal end 11 of access port 10. Filter 50 is deployed in aorta 100 by advancing filter shaft 55 distal to access port 10. Expandable balloon occluder 65 is mounted proximal to port 63 on catheter 56. Port 63 communicates with a lumen which is adapted for infusion of cardioplegia solution. The occluder and the filter are operated independent of each other. Other embodiments of the device carrying an occlusion member and a filter include the following: (1) having a dam covering the opening of the filter, (2) having two filters, one of which functions as an occluder, (3) having a balloon occluder mounted on the center of the filter shaft, (4) having a balloon surrounded by an inflatable seal as the occlusion member, (5) having a dam and an inflatable seal, and (6) having the occlusion member and filter constructed as a colander which can be operated to completely or partially occlude the aortic lumen.

FIGS. 12A, 12B, and 12C depict another embodiment of the device carrying an occlusion member and a blood filter. In FIG. 12A, elongate tube 70 is housed within lumen 34 of the medical device. The tube has lumen 71 which communicates with balloon occluder 65 at a distal end. Filter 50 is mounted at distal region 72 of the tube proximal to the occluder and is in a compressed state inside lumen 34. The distal region includes bendable region 74. Distal region 72 assumes a linear configuration relative to its proximal end when housed within the lumen of the device, and assumes a preformed angled configuration relative to its proximal end when protruding distal to port 33 of the device.

In use, the device is inserted through proximal end 11 of access port 10 included in the cannula system of FIG. 1, which is inserted in aorta 100. As catheter 70 is advanced distally through port 33 of the device and access port 10, the distal region of the catheter assumes its preformed angled configuration relative to its proximal end. The frame for filter 50, which may be constructed of elastic material, e.g., plastic or nitinol, is expanded from its compressed state to contact the aortic wall. Balloon occluder 65 is expanded to occlude the aortic lumen by infusing air or fluid through lumen 71 of the catheter. Oxygenated blood can then be infused through lumen 6 and port 5 of cannula 1 downstream in the aorta to establish cardiopulmonary bypass.

Figure 12E:
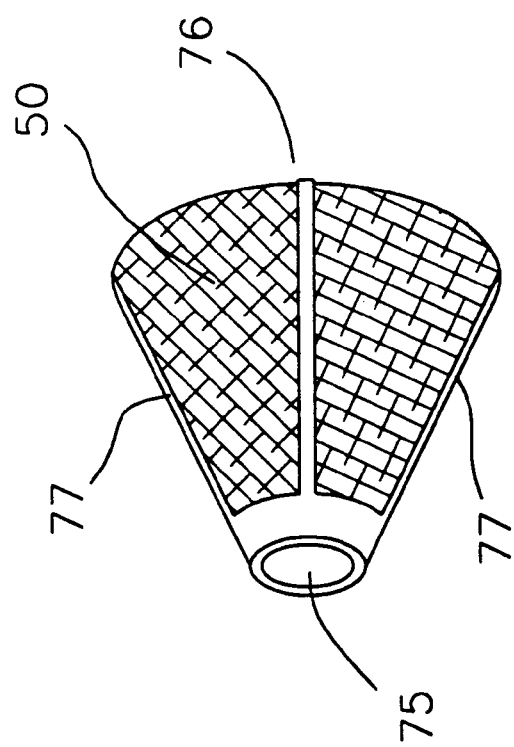
FIG. 12E depicts the filter of FIG. 12D in an expanded state.
Figure 12D:
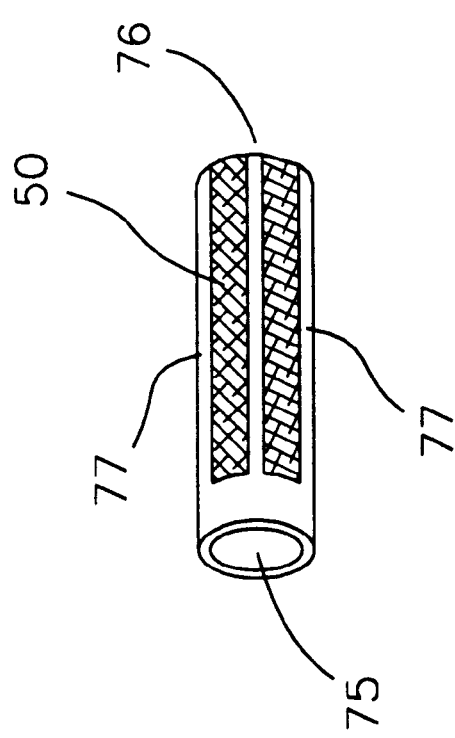
FIG. 12D depicts the filter in the device of FIG. 12A, the filter in a compressed state.

After the surgeon has performed the procedure and cardiac arrest is reversed, balloon occluder 65 is deflated as depicted in FIG. 12C. Embolic material generated during the procedure is captured by filter 50, thereby preventing distal embolization to peripheral organs causing tissue ischemia or death. The entrapped emboli are removed from the aorta by retracting catheter 70 proximally and compressing filter 50 within the lumen of the device. One embodiment of filter 50 in a compressed state is shown in FIG. 12D. The filter device comprises a compliant expandable framework having proximal opening 75 and distal opening 76. The framework is mounted on the distal end of a catheter at the proximal opening. The framework includes struts 77, which are made of flexible materials, e.g., plastic or shape memory materials, such as nitinol, and blood filter 50. FIG. 12E depicts the filter of FIG. 12D in an expanded state when the compliant framework is not under any external compressing force.

Figure 13:
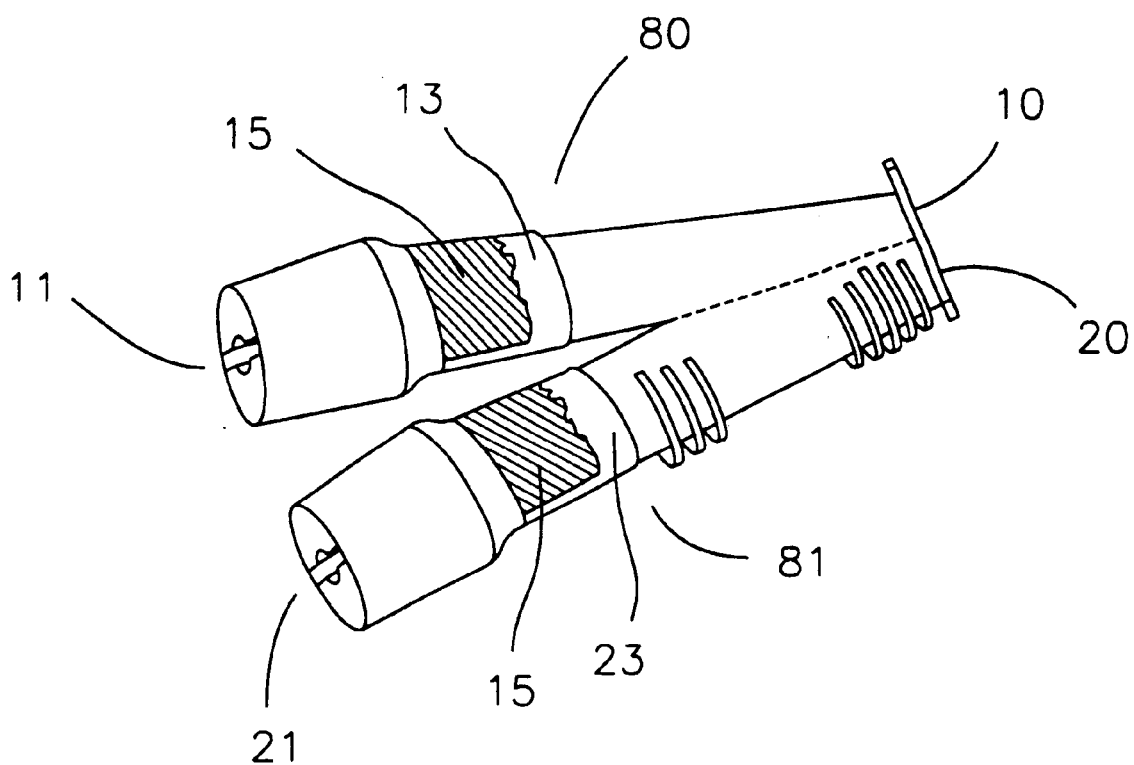
FIG. 13 depicts a multi-port introducer having two lumens.

FIG. 13 depicts one embodiment of a multi-port introducer for introducing medical devices into a vessel. The introducer comprises first tubular member 80 and second tubular member 81 mounted adjacent the first member. The first tubular member has lumen 13 communicating with proximal end 11 and distal port 10. The second member has lumen 23 communicating with proximal end 21 and distal port 20. In some embodiments, lumens 13 and 23 of the respective first and second tubular member may merge and communicate at their distal ends. Hemostatic valves 15 are disposed within the lumen of each tubular member to prevent blood escaping from the proximal ends after insertion in a vessel. Other embodiments of the multi-port introducer may include 3, 4, 5, or more lumens and ports for introduction of medical devices, including a blood filter, an occlusion catheter, an aspirator, an angioplasty catheter, a valvuoplasty catheter, an electrode catheter, internal vessel segregating or isolating dams, an endoscopic camera, a pressure monitor, a stent, a graft, a shunt, a perfusion catheter, and endoscopic devices.

Figure 14A:
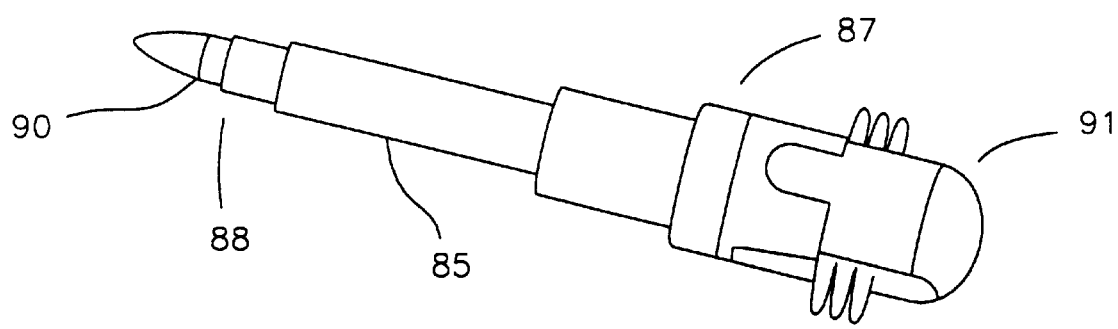
FIG. 14A depicts a vessel introducer.
Figure 14B:
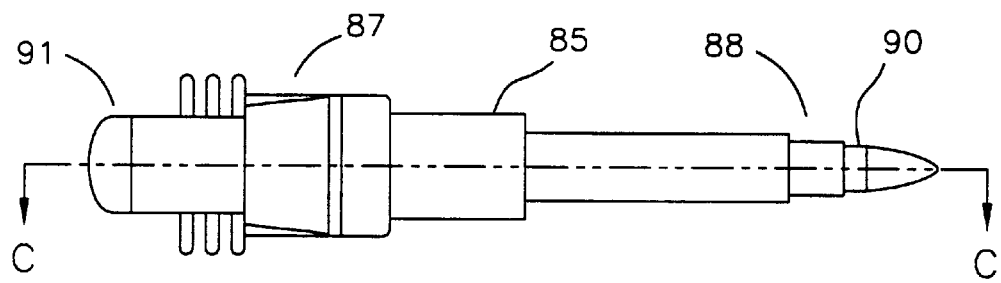
FIG. 14B depicts a lateral view of the introducer of FIG. 14A.
Figure 14C:
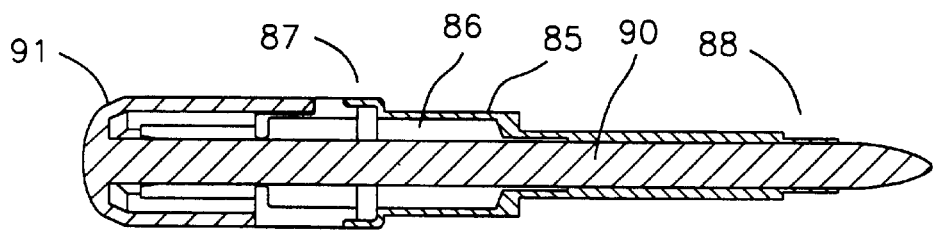
FIG. 14C depicts a cross-sectional view of the introducer through section line C—C of the introducer depicted in FIG. 14B.

FIGS. 14A, 14B, and 14C depict one embodiment of a vessel introducer comprising tubular member 85 and obturator 90. The tubular member has lumen 86 communicating with proximal end 87 and distal end 88. Obturator 90 which includes proximal end 91 is removably inserted in lumen 86 of the tubular member as depicted in FIG. 14C.

FIGS. 15A, 15B, 15C, and 15D depict further details of tubular member 85 of the vessel introducer. Lumen 86 communicates with port 89 at distal end 88. When the obturator is inserted in the tubular member, a distal end of the obturator protrudes distal to port 89. FIGS. 15B and 15C provide, respectively, proximal and distal views of the tubular member shown in FIG. 15A.

FIG. 16A depicts a lateral view of the obturator of FIG. 14B. Proximal end 91, connected to body 92 of the obturator, includes releasable engaging mechanism 36, depicted as a latch in FIG. 16B. Gripping members 37 are mounted proximal to the engaging mechanism 36 on opposite sides of the obturator. The engaging mechanism is operated by depressing the gripping members radially inward for insertion into the tubular introducer. FIG. 16C depicts a cross-sectional view of the obturator through section line C—C of the obturator in FIG. 16A. FIG. 16D depicts a distal view of the obturator of FIG. 16A. In certain embodiments the obturator is equipped with porous plug 38 which communicates with hollow channel 93. In this embodiment gas is vented from the port of the access cannula through hollow channel 93 and plug 38, thereby purging the port of gas and making the port ready for introduction of therapeutic instruments.

Figure 17A:
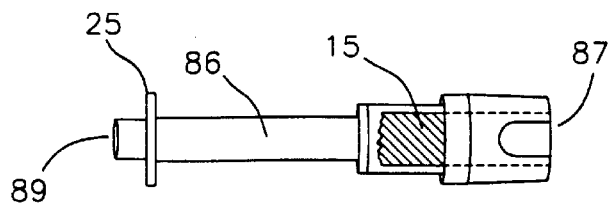
FIG. 17A depicts another embodiment of the tubular member of the vessel introducer.
Figure 17B:
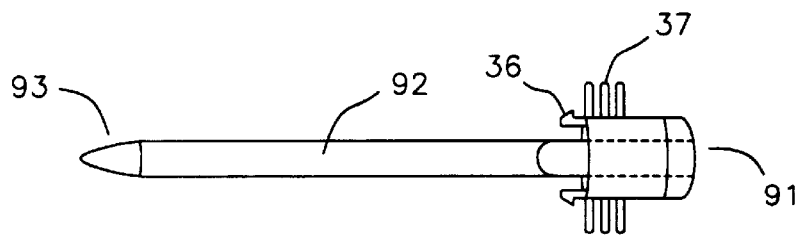
FIG. 17B depicts another embodiment of the obturator of the vessel introducer.

FIG. 17A depicts another embodiment of the tubular member having suture flange 25. Lumen 86, communicating with port 89 and proximal end 87, includes hemostatic valve 15. FIG. 17B depicts another embodiment of the obturator having an elongate body 92 connected to distal end 93 and proximal end 91. The obturator has releasable engaging mechanism 36 similar to that of FIG. 16B.

Figure 17C:
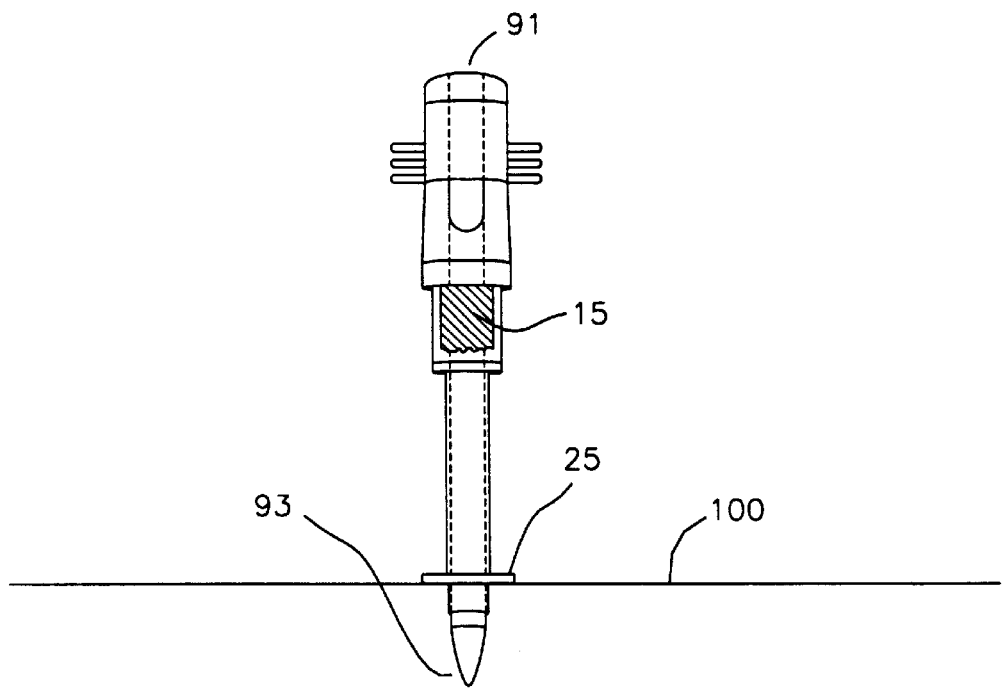
FIG. 17C depicts the vessel introducer of FIG. 17A and obturator of FIG. 17B inserted in the aorta.
Figure 17E:
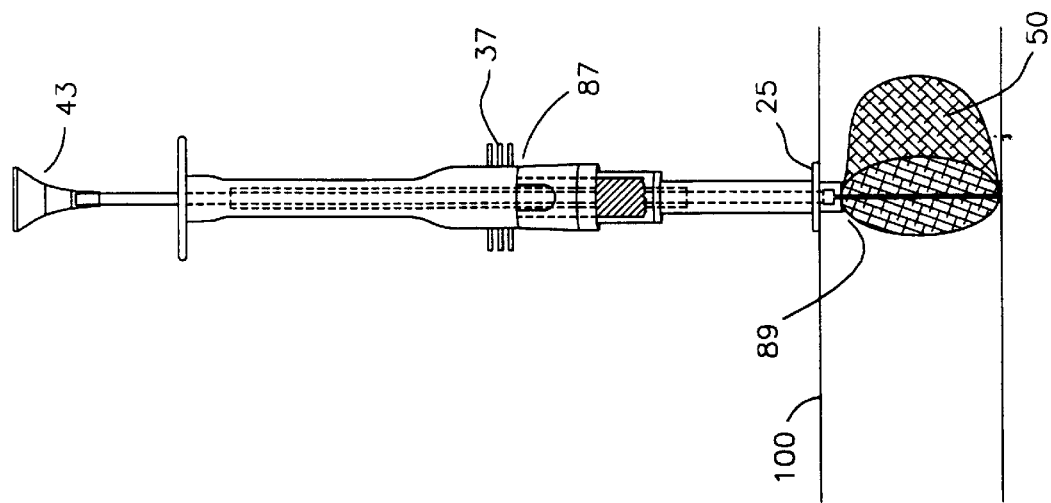
FIG. 17E depicts the filter of FIG. 6A inserted in the tubular member of FIG. 17D.
Figure 17D:
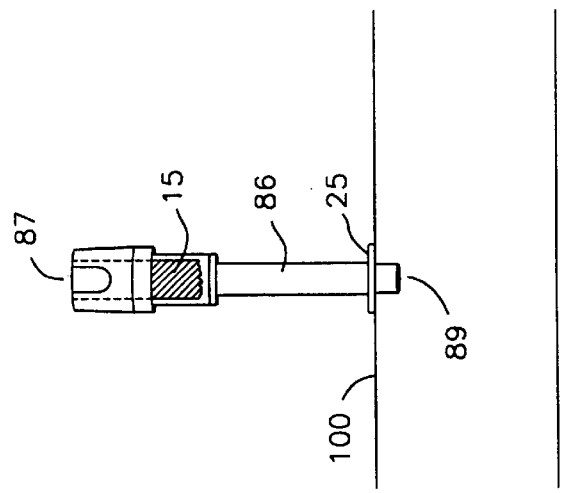
FIG. 17D depicts the tubular member of FIG. 17A inserted in the aorta.

In use, the obturator is inserted through proximal end 87 and lumen 86 of the tubular member, where distal end 93 of the obturator protrudes from distal port 89 of the tubular member. The assembled vessel introducer is inserted through an incision on aorta 100 as depicted in FIG. 17C. Sutures can be placed between suture flange 25 and the aortic wall to stabilize the introducer. The obturator is then removed from the tubular member, leaving proximal end 87, lumen 86, and port 89 ready to receive a medical device as shown in FIG. 17D. In FIG. 17E, the device of FIG. 6A carrying blood filter 50 is shown inserted through the proximal end and lumen of the tubular member, where the filter protrudes distal of port 89 to deploy in the aortic lumen. The filter can be temporarily removed by pulling proximal end 43 of the device proximally when surgical space within the aortic lumen is limited, e.g., during aortic valve replacement surgery. The filter can then be redeployed to entrap embolic materials generated during the procedure.

Figure 18:
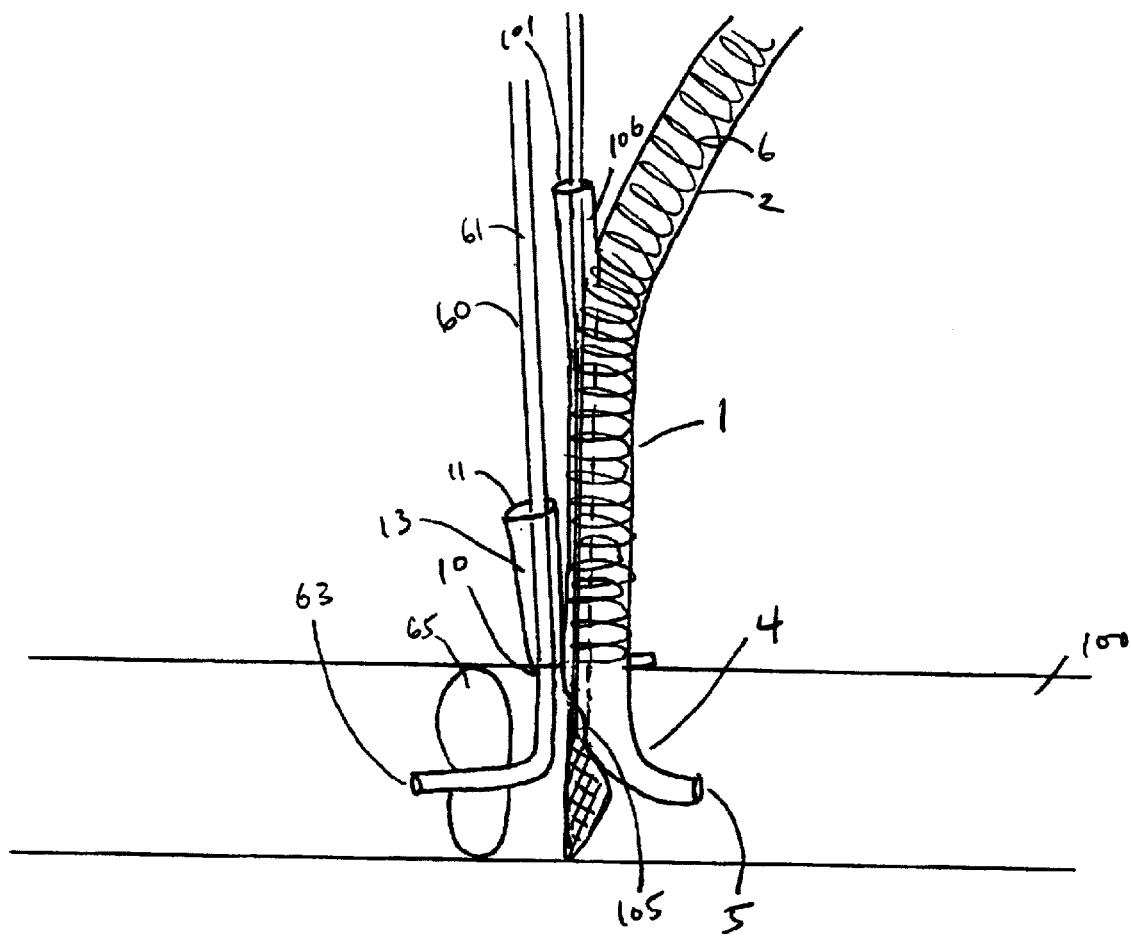
FIG. 18 depicts another embodiment of the cannula system having a side-port on the cannula.

FIG. 18 depicts another embodiment of the cannula system inserted in aorta 100. The system includes access port 10 mounted adjacent to cannula 1. The cannula comprises elongate member 2 having lumen 6 and lumen 106. Lumen 6 communicates with distal port 5. Lumen 106 communicates proximally with proximal end 101 and distally either with side-port 105 or lumen 6. Lumen 106 and port 105 are adapted for deployment of medical therapies, such as the blood filter of FIGS. 6A and 6B, shown here inserted through proximal end 101. Catheter 60, having expandable occlusion balloon 65 mounted on the distal end, is inserted through proximal end 11 and lumen 13 of access port 10.

In using the cannula system for cardiopulmonary bypass, cannula 1 and access port 10 are inserted into ascending aorta 100. Balloon 65 is inflated to occlude the aortic lumen. Port 63, which communicates with lumen 61 of catheter 60, can be used to deliver cardioplegia solution upstream to the coronary arteries to arrest the heart. Oxygenated blood can be delivered to the aorta downstream to perfuse the peripheral organs through lumen 6 and port 5 of cannula 1. The blood filter can be inserted through proximal end 101, lumen 106, and port 105 to deploy in the aorta to capture embolic material generated during cardiac procedures. In this way, the cannula system allows delivery of multiple medical therapies to the aorta through one incision, thereby minimizing trauma to the aortic wall.

The length of the cannula will generally be between 10 and 60 centimeters, more preferably approximately 20 to 35 centimeters, more preferably approximately 30 centimeters. The inner diameter of the cannula will generally be between 0.5 and 1.5 centimeters, preferably approximately 1.0 centimeters. The length of the modular access port will generally be between 2.0 and 10.0 centimeters, preferably approximately 6.0 centimeters. The inner diameter of the lumen of the access port will generally be between 0.2 and 1.2 centimeters, preferably approximately 0.6 centimeters. The length of the vessel introducer will generally be between 6 and 14 centimeters, preferably approximately 9 centimeters. The inner diameter of the lumen of vessel introducer will generally be between 0.2 and 1.2 centimeters, preferably approximately 0.5 centimeters. The foregoing ranges are set forth solely for the purpose of illustrating typical device dimensions. The actual dimensions of a device constructed according to the principles of the present invention may obviously vary outside of the listed ranges without departing from those basic principles.

Although the foregoing invention has, for purposes of clarity of understanding, been described in some detail by way of illustration and example, it will be obvious that certain changes and modifications may be practiced which will still fall within the scope of the appended claim.

What is claimed is:

1. A method for cannulation of a patient's blood vessel or cardiac tissue, comprising the steps of:
    making an incision on the aortic arch;
    providing an arterial return cannula having an arterial return lumen and a first port and a second port adjacent a distal end;
    inserting the distal end of the cannula through the incision into a vessel or cardiac tissue;
    infusing oxygenated blood through the arterial return lumen;
    inserting a first medical device through the first port into the vessel or cardiac tissue such that the first medical device extends beyond the first port;
    inserting a second medical device through the second port into the vessel or cardiac tissue such that the second medical device extends beyond the second port;
    deploying the first medical device; and
    deploying the second medical device.

2. The method of claim 1, wherein the first medical device is selected from the group consisting of a blood filter, an occlusion catheter, an aspirator, an angioplasty catheter, a valvuloplasty catheter, an electrode catheter, internal vessel segregating or isolating dams, an endoscopic camera, a pressure monitor, a stent, a graft, a shunt, a perfusion catheter, and endoscopic devices.

3. The method of claim 1, wherein the vessel is an artery.

4. The method of claim 1, wherein the artery is the aorta.

5. The method of claim 1, wherein the cardiac tissue is the right atrium.

6. The method of claim 1, wherein the vessel is a vein.

7. The method of claim 6, wherein the vein is the inferior vena cava.

8. The method of claim 1, wherein the second medical device is selected from the group consisting of a blood filter, an occlusion catheter, an aspirator, an angioplasty catheter, a valvuloplasty catheter, an electrode catheter, internal vessel segregating or isolating dams, an endoscopic camera, a pressure monitor, a stent, a graft, a shunt, a perfusion catheter, and endoscopic devices.

9. A method for cannulation of a patient's blood vessel or cardiac tissue, comprising the steps of:
    providing an arterial return cannula having an arterial return lumen and a first port and a second port adjacent a distal end;
    inserting the distal end of the cannula into a vessel or cardiac tissue;
    infusing oxygenated blood through the arterial return lumen;
    inserting a first medical device through the first port into the vessel or cardiac tissue such that the first medical device extends beyond the first port;
    inserting a second medical device through the second port into the vessel or cardiac tissue such that the second medical device extends beyond the second port;
    deploying the first medical device; and
    deploying the second medical device.

10. The method of claim 9, wherein the first and medical device are selected from the group consisting of a blood filter, an occlusion catheter, an aspirator, an angioplasty catheter, a valvuloplasty catheter, an electrode catheter, internal vessel segregating or isolating dams, an endoscopic camera, a pressure monitor, a stent, a graft, a shunt, a perfusion catheter, and endoscopic devices.

11. The method of claim 9, wherein the vessel is an artery.

12. The method of claim 11, wherein the artery is the aorta.

13. The method of claim 9, wherein the cardiac tissue is the right atrium.

14. The method of claim 9, wherein the vessel is a vein.

15. The method of claim 14, wherein the vein is the inferior vena cava.

* * * * *